US010078897B2

United States Patent
Shupp et al.

(10) Patent No.: US 10,078,897 B2
(45) Date of Patent: Sep. 18, 2018

(54) SYSTEMS AND METHODS FOR IDENTIFYING BURN WOUND CONVERSION

(71) Applicant: Medstar Health, Columbia, MD (US)

(72) Inventors: Jeffrey W. Shupp, Columbia, MD (US); Nicholas J. Prindeze, Columbia, MD (US); Lauren T. Moffatt, Columbia, MD (US)

(73) Assignee: MEDSTAR HEALTH, Columbia, MD (US)

( * ) Notice: Subject to any disclaimer, the term of this patent is extended or adjusted under 35 U.S.C. 154(b) by 247 days.

(21) Appl. No.: 15/137,304

(22) Filed: Apr. 25, 2016

(65) Prior Publication Data

US 2016/0321804 A1 Nov. 3, 2016

Related U.S. Application Data

(60) Provisional application No. 62/152,109, filed on Apr. 24, 2015.

(51) Int. Cl.
*G06T 7/00* (2017.01)
*A61B 5/00* (2006.01)

(52) U.S. Cl.
CPC .......... *G06T 7/0016* (2013.01); *A61B 5/0077* (2013.01); *A61B 5/445* (2013.01); *G06T 2207/10048* (2013.01); *G06T 2207/30088* (2013.01); *G06T 2207/30096* (2013.01)

(58) Field of Classification Search
CPC ..... A61B 5/0077; A61B 5/445; G06T 7/0016; G06T 2207/10048; G06T 2207/30088; G06T 2207/30096
See application file for complete search history.

(56) References Cited

U.S. PATENT DOCUMENTS

| 5,074,306 A | * | 12/1991 | Green | A61B 5/0071 600/317 |
| 2014/0213910 A1 | * | 7/2014 | Durkin | A61B 5/0075 600/477 |
| 2014/0276358 A1 | * | 9/2014 | Kashiwagi | A61N 5/0616 604/20 |
| 2014/0316387 A1 | * | 10/2014 | Harris | A61K 41/0047 606/3 |
| 2017/0296697 A1 | * | 10/2017 | Fraser | A61L 27/24 |

OTHER PUBLICATIONS

Modalities for the Assessment of Burn Wound Depth.*
Endothelial necrosis at 1 h post-burn predicts progression of tissue injury.*
Burn depths evaluation based on active dynamic IR thermal imaging—A preliminary study.*
Active Dynamic Infrared Thermal Imaging in Burn Depth Evaluation.*

* cited by examiner

*Primary Examiner* — Zhihan Zhou
(74) *Attorney, Agent, or Firm* — Tarolli, Sundheim, Covell & Tummino LLP (57) ABSTRACT

One aspect of the present disclosure describes a method for burn wound assessment that identifies burn wound conversion. The method includes performing non-contact imaging on the burn wound with an imaging modality configured to record imaging data. The imaging modality includes active dynamic thermography (ADT). Based on the imaging data, an area of the burn wound undergoing conversion can be determined. The determination can be accomplished automatically by a system comprising a processor.

15 Claims, 10 Drawing Sheets

SYSTEMS AND METHODS FOR IDENTIFYING BURN WOUND CONVERSION

RELATED APPLICATIONS

This application claims the benefit of U.S. Provisional Application No. 62/152,109, filed Apr. 24, 2015, entitled "ACTIVE DYNAMIC THERMOGRAPHY IS A SENSITIVE METHOD FOR DISTINGUISHING BURN WOUND CONVERSION." The entirety of this provisional application is hereby incorporated by reference for all purposes.

FIELD OF THE INVENTION

The present disclosure relates generally to burn wound assessment and, more particularly, to systems and methods that can identify areas of burn wound conversion using an imaging modality.

BACKGROUND OF THE INVENTION

The Jackson model of a burn wound provides concentric zones related to the burn wound: the zone of necrosis, the zone of stasis, and the zone of hyperemia. According to the Jackson model, tissue within the central zone of necrosis is entirely non-viable, while tissue within the external zone of hyperemia will recover from the burn. However, tissue within the zone of stasis is potentially viable, but risks undergoing burn wound conversion, in which the initially viable tissue converts to necrotic tissue. Burn wound conversion may be a significant contributor to the morbidity of burn wounds. However, burn wound conversion remains a unique and challenging problem in burn wound assessment at least because there is no accurate, objective, and non-invasive measurement to predict and/or identify burn wound conversion.

SUMMARY OF THE INVENTION

The present disclosure relates generally to burn wound assessment and, more particularly, to systems and methods that can identify areas of burn wound conversion using an imaging modality. For example, the imaging modality can be active dynamic thermography (ADT).

In one aspect, the present disclosure can include a method for burn wound assessment that identifies burn wound conversion. The method can include performing non-contact imaging on a burn wound with an imaging modality configured to record imaging data. For example, the imaging modality can include ATD. Based on the imaging data, an area of the burn wound undergoing conversion can be determined. In some instances, the prediction can be accomplished by a system comprising a processor.

In another aspect, the present disclosure can include an ADT diagnostic device. The device can include a thermal stimulator to deliver thermal stimulation to a burn wound. The device can also include a controller to control properties related to the thermal stimulation. For example, the properties can include a timing parameter of the thermal stimulation. The device can also include a receiver to receive imaging data based on the thermal stimulation of the burn wound. The imaging data can indicate an area of the burn wound undergoing conversion.

In a further aspect, the present disclosure can include a system that can be used to perform burn wound assessment. The system can include an imaging device and a computing device. The imaging device can be used to perform non-contact imaging on a burn wound. The imaging modality can be configured to record imaging data. For example, the imaging modality can be ADT. The computing device can include a non-transitory memory to store computer-executable instructions and a processor to access the non-transitory memory and execute the computer-executable instructions to at least: receive the imaging data; and determine an area of the burn wound undergoing conversion based on the imaging data.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION OF THE INVENTION

I. Definitions

In the context of the present disclosure, the singular forms "a," "an" and "the" can also include the plural forms, unless the context clearly indicates otherwise.

The terms "comprises" and/or "comprising," as used herein, can specify the presence of stated features, steps, operations, elements, and/or components, but do not preclude the presence or addition of one or more other features, steps, operations, elements, components, and/or groups.

As used herein, the term "and/or" can include any and all combinations of one or more of the associated listed items.

Additionally, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or acts/steps) is not limited to the order presented in the claims or figures unless specifically indicated otherwise.

As used herein, when two or more devices are "coupled", a connection is established between the two or more devices. The connection can be wired, wireless, or a combination of wired and wireless. For example, respective wireless transmitters, receivers, or transceivers can be used to establish a wireless connection between the two or more devices.

As used herein, the term "computing device" can refer to a device that includes a non-transitory memory that stores instructions and a processor configured to execute the instructions to facilitate performance of one or more operations. In some instances, the non-transitory memory can also store data corresponding to the one or more operations.

As used herein, the term "imaging modality" a particular mode for recording imaging data related to a measurement location (e.g., a portion of a patient's body). In some instances, the imaging modality can be a non-contact imaging modality, in which imaging is accomplished without touching the portion of the patient's body. Examples of non-contact imaging modalities can include active dynamic thermography (ADT), laser Doppler imaging (LDI), and the like.

As used herein, the terms "burn" and "burn wound" refer to an injury to tissue (e.g., skin) caused by heat, friction, electricity, radiation, or chemicals. A burn can be represented by the Jackson burn wound model, which considers the effect of secondary injury on burns. The Jackson model provides concentric zones, each with a different effect. The zone of necrosis is the central zone with tissue that is most severely damaged and irreversibly lost. The zone of stasis is outside the zone of necrosis and contains tissue that can potentially recover, but also may be converted to necrotic tissue. The zone of hyperaemia is the most peripheral zone that includes tissue that will recover.

As used herein, the terms "burn wound conversion," "burn wound progression," and "conversion" can refer to the process by which certain superficial portions of a burn (e.g., within the zone of stasis) spontaneously undergo necrosis.

As used herein, the term "medical professional" can refer to any person involved the conducting a burn wound assessment, including, but not limited to, physicians, residents, medical students, nurse practitioners, nurses, nursing students, and other medical staff.

As used herein, the term "patient" can refer to any warm-blooded organism including, but not limited to, a human being, a pig, a rat, a mouse, a dog, a cat, a goat, a sheep, a horse, a monkey, an ape, a rabbit, a cow, etc.

II. Overview

The present disclosure relates generally to burn wound assessment. One challenge with regard to burn wound assessment is the development of burn wound conversion. Such burn wound conversion can be a significant contributor to burn wound morbidity; however, previously, it has been impossible to determine areas of the burn would that are undergoing conversion at an early stage. Accordingly, the present disclosure relates, more particularly, to systems and methods that can identify these areas of burn wound conversion using an imaging modality. The imaging modality can provide a quantitative measurement to identify these areas of burn wound conversion during an early assessment of the burn wound (e.g., within 12 hours of the burn wound).

The imaging modality can be a non-contact diagnostic technique for the early assessment of burns wounds. For example, the imaging modality can be active dynamic thermography (ADT), which can resolve the three-dimensional structure of the burn wound through heat transfer analysis. Since burn wound conversion is a product of physiological changes in the three dimensional structure with significant modification of heat transfer properties. For example, ADT can be used to deliver a thermal pulse to the burn wound on the skin surface and detect properties related to heat transfer through the burn wound (e.g., thermal conductivity—the rate of transfer of a thermal pulse through the dermal capillary network and to the dermal plexus below). When ADT is performed over time, changes in the properties related to heat transfer can be seen in certain areas that are undergoing conversion. Accordingly, ADT can specifically identify areas undergoing the process of burn wound conversion and serve as an important tool for burn wound care.

III. Systems

One aspect of the present disclosure can include a system 10 (FIG. 1) that can identify areas of burn wound conversion. As noted, the Jackson model provides concentric zones related to the burn wound, including the central zone of necrosis and the external zone of hyperemia with the zone of stasis therebetween. Tissue within the zone of stasis is potentially viable, but risks undergoing burn wound conversion. Advantageously, the system 10 can identify tissue within the zone of stasis undergoing burn wound conversion earlier than traditional treatments. For example, the system 10 can identify the burn wound conversion within 12 hours post-injury. With the identification of the burn wound conversion, the system 10 can facilitate the design of a treatment for the burn wound (e.g., a surgical excision of the necrotic tissue and converting tissue at an earlier time than traditional treatments) that is tailored for the specific patient. Additionally, earlier identification of the burn wound conversion can reduce burn-related morbidity, including wound contracture, infection, and the likelihood of scarring and pigmentation.

Figure 1:
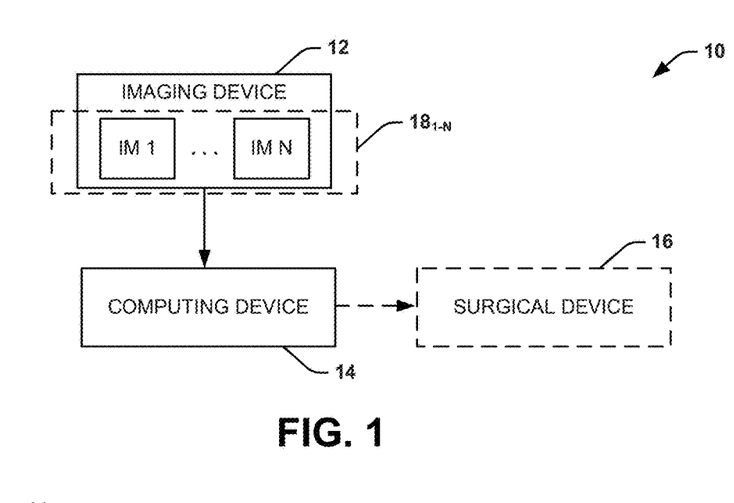
FIG. 1 is a block diagram of a system that can identify areas of burn wound conversion using an imaging modality in accordance with an aspect of the present disclosure.

The system 10 can employ an imaging device 12 and a computing device 14 to identify the areas undergoing burn wound conversion. The imaging device 12 can include at least one imaging modality $18_{1-N}$ that can perform non-contact imaging of a burn wound and record imaging data that includes a time series progression that illustrates burn wound conversion development. Non-contact imaging provides clear advantages in identifying areas of burn wound conversion because it is easy to use and provides quantitative data. The imaging modalities $18_{1-N}$ can include one or more functional imaging modalities and/or one or more structural imaging modalities.

In some instances, the imaging modalities $18_{1-N}$ can include active dynamic thermography (ADT), which can detect thermal conductivity in the different zones of the burn wound. Generally, ADT delivers a thermal pulse to the surface of the skin and records the rate of dissipation of the pulse through the dermal capillary network and the dermal plexus below, which directly relates to the sub-surface resistance to heat transfer. Accordingly, following the thermal stimulation, the energy emitted in the form of radiation over time ($q_R$) is proportional to the energy transferred to and removed by the dermal plexus ($q_C$). Because the thermal conductivity (k) of the zone of stasis is greater than that of the zone of necrosis, the rate of energy transferred to the dermal plexus would be proportionally greater according to Fourier's law. The rate of energy emitted at the surface will therefore be greater for the zone of stasis than that of necrosis. Using this general principle, ADT can identify and quantify areas within the zone of stasis that are undergoing conversion by examining temporal changes in the thermal conductivity of the tissue.

Figure 2:
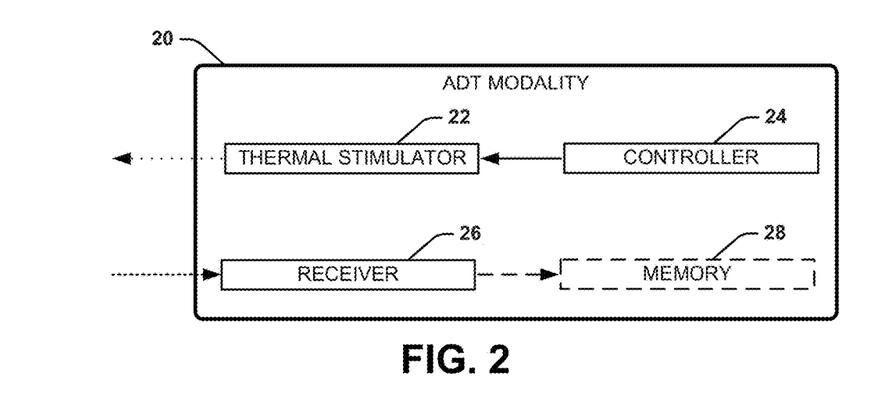
FIG. 2 is a block diagram of an example imaging modality that can be used by the imaging device of the system shown in FIG. 1.

In some examples, a device to deliver ADT can improve upon its predecessors by allowing precise, sub-millisecond control of thermal stimulation. An example of an ADT modality 20 that can be used in the imaging device 12 is shown in FIG. 2. The ADT modality 20 can include a thermal stimulator 22 to deliver a thermal stimulation to the burn wound. In some instances, the thermal stimulator 22 can include one or more stimulation lamps or other mechanisms to deliver an infrared pulse to the tissue. Properties related to the thermal stimulation delivered by the thermal stimulator 22 can be set by a controller 24. For example, the properties can include a timing parameter, which the controller 24 can set less than 50 milliseconds, less than 10 milliseconds, less than 5 milliseconds, or less than 1 millisecond. In other words, the controller 24 can determine when and how often the thermal stimulator 22 delivers the thermal stimulation.

The ADT modality 20 can also include a receiver 26 that can receive the imaging data in response to the thermal stimulation. In some instances, the receiver 26 can include a thermal camera. In other instances, the receiver 26 can also include a data acquisition control system. Optionally, the ADT modality 20 can include a non-transitory memory 28 to store the recorded data. The non-transitory memory 28 can, additionally or alternatively, store a calibration model.

It will be noted, however, that ADT alone may not be the sole solution for total burn assessment. As an example, the imaging modalities $18_{1-N}$ can include active dynamic thermography (ADT) and laser Doppler imaging (LDI), each with identifies different characteristics of a burn wound. For example, ADT can detect areas undergoing conversion, while LDI can detect areas undergoing healing.

Figure 3:
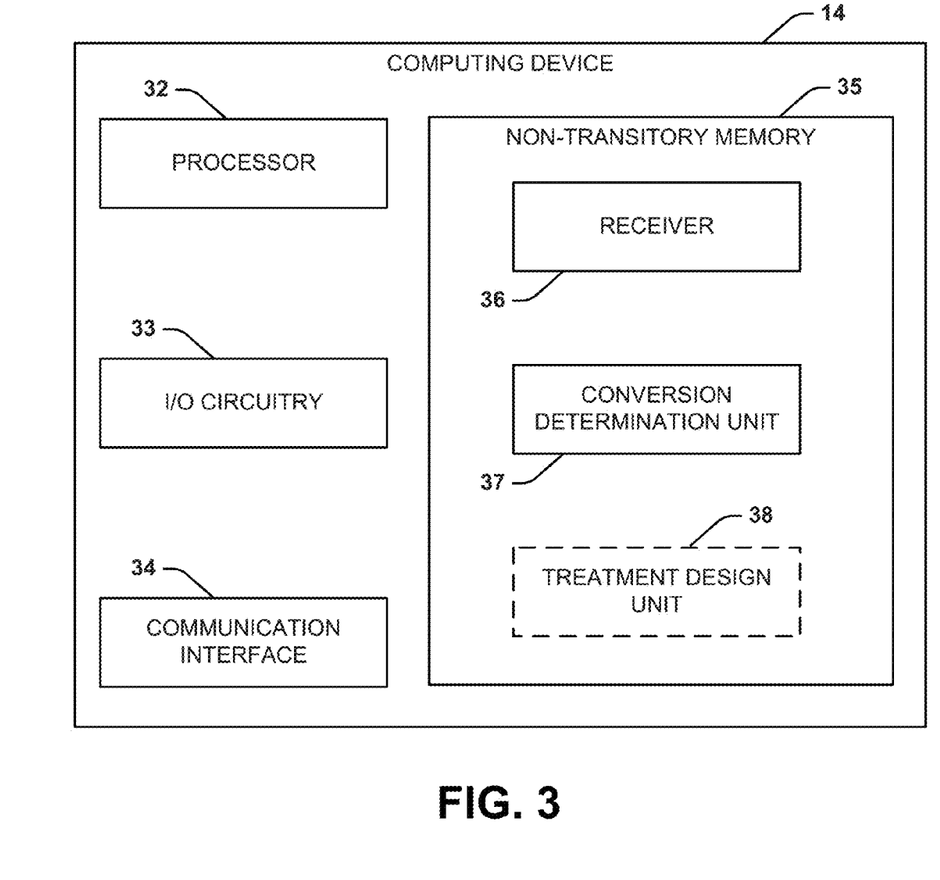
FIG. 3 is a block diagram of an example computing device that can be used in the system shown in FIG. 1.

The system 10 can also include a computing device 14 that can process the imaging data and determine the areas undergoing conversion. In some instances, the computing device 14 can be included within the imaging device 12. In other instances, the computing device 14 can be remote from the imaging device 12 and coupled to the imaging device 12. An example of the computing device 14 is shown in FIG. 3. In this example, the computing device 14 can include a processor 32, I/O circuitry 33 a communication interface 34, and a non-transitory memory 35. The non-transitory memory can store data and computer-executable instructions that can be executed by the processor 32. The computer executable instructions can include a receiver 36 and a conversion determination unit 37. The receiver 36 can receive the imaging data from the imaging modality $18_{1-N}$. In some instances, the receiver 36 can perform one or more signal processing tasks on the imaging data. The conversion determination unit 37 can determine the area of the burn wound undergoing conversion based on the imaging data. The determination can be made based on a structural change in the area undergoing the burn wound conversion that is evident within the imaging data. For example, the conversion determination unit 37 can determine the area of the burn wound undergoing conversion based on an associated rate of heat transfer relative to a rate of heat transfer in another area of the burn wound (e.g., different areas in the zone of stasis).

In some instances, optionally, the computer-executable instructions can also include a treatment design unit 38. The treatment design unit 38 can design a treatment for the burn wound based on the identified area of burn wound conversion. In some instances, the treatment design unit 38 can also consider healthy areas (e.g., detected by LDI) in the design of the treatment. For example, the treatment can be designed so that the areas of necrosis, along with the converting areas are excised, while healthy areas remain in place. As illustrated in FIG. 1, another optional feature is a surgical device that can be coupled to the computing device to facilitate the execution of the treatment plan.

IV. Methods

A second aspect of the present disclosure can include a method 40 (FIG. 4) for identifying areas of burn wound conversion using an imaging modality. In some instances, the imaging modality can be active dynamic thermography (ADT), which can specifically identify the processes of burn wound conversion and serve as an important tool for burn care. In some instances, one or more steps of the method 40 can be performed by elements of the system 10 as shown in FIG. 1.

Figure 4:
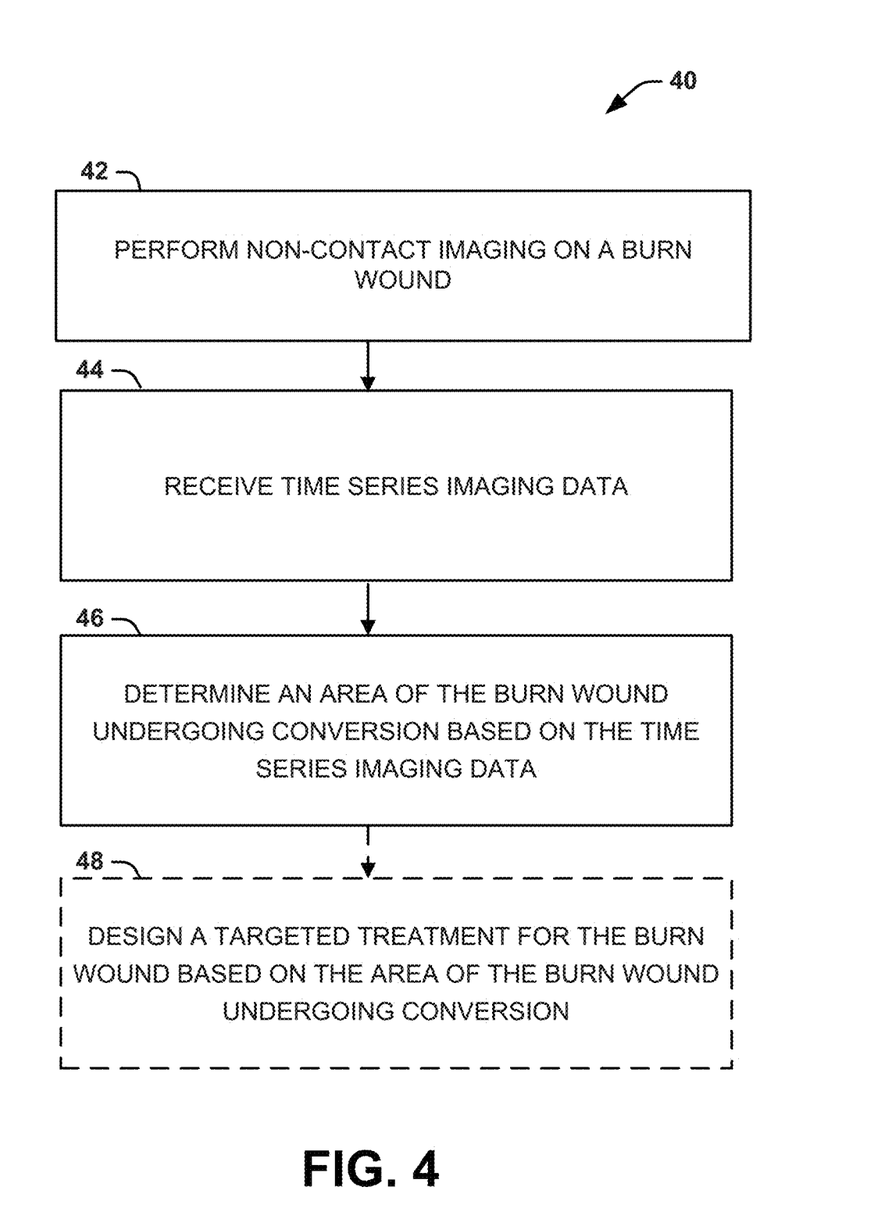
FIG. 4 is a process flow diagram of a method for identifying areas of burn wound conversion using an imaging modality, according to another aspect of the present disclosure.

The method 40 is illustrated as process flow diagrams with flowchart illustrations. For purposes of simplicity of explanation, the method 40 is shown and described as executing serially, it is to be understood and appreciated that the present disclosure is not limited by the illustrated order, as some aspects could occur in different orders and/or concurrently with other aspects shown and described herein. Moreover, not all illustrated aspects may be required to implement method 40.

In some instances, one or more blocks of the respective flowchart illustrations, and combinations of blocks in the block flowchart illustrations, can be implemented by computer program instructions. These computer program instructions can be stored in memory and provided to a processor of a general purpose computer, special purpose computer, and/or other programmable data processing apparatus to produce a machine, such that the instructions, which execute via the processor of the computer and/or other programmable data processing apparatus, create mechanisms for implementing the steps/acts specified in the flowchart blocks and/or the associated description. In other words, some of the steps/acts can be implemented by a system comprising a processor that can access the computer-executable instructions that are stored in a non-transitory memory.

Referring now to FIG. 4, at element 42, non-contact imaging can be performed on a burn wound. The non-contact imaging can be performed by an imaging modality (e.g., $IM_{1-N}$ 18 of imaging device 12) configured to record imaging data. For example, the imaging modality can be ADT (e.g., ADT modality 20). ADT can include the delivery of a thermal pulse to the burn wound. The resulting image data can relate to heat transfer for areas being imaged over time. At 44, the time series imaging data can be received (e.g., by receiver 36 of computing device 14).

At 46, an area of the burn wound undergoing conversion can be determined (e.g., by conversion determination unit 37) based on the time series imaging data. The determination can include an identification of structural changes corresponding to the area of the burn wound undergoing conversion. For example, the area of the burn wound undergoing conversion can be located within the zone of stasis of the burn wound. The area of the burn wound undergoing conversion can be identified based on a slower rate of heat transfer being exhibited compared to the rest of the areas in the zone of stasis. In other words, the rate of heat transfer can reflect a dissipation of the thermal pulse through a dermal capillary network and to a dermal plexus below the burn wound.

Optionally, at 48, a targeted treatment can be designed for the burn wound based on the area of the burn wound undergoing conversion. For example, the targeted treatment can include a specific surgical procedure (e.g., using surgical device 16) relating to excision of necrotic tissue, including the area of the burn wound undergoing conversion. The aim of the targeted treatment can be to excise all of the necrotic tissue while preserving all of the viable tissue.

V. Example

The following example illustrates that ADT can be used to identify structural changes representing burn wound conversion. For example, as shown, ADT can detect burn wound conversion as early as 12 hours post-injury.

Methods

Imaging Calibration Phantom

In order to determine the optimal stimulation parameters of this custom designed ADT device, an imaging calibration phantom was prepared by mounting a series of stainless steel washers within paraffin wax at depths ranging from 0-8 mm, to assess visibility of depth. The inner and outer diameter of the stainless steel (k=15 W/mK15) washers ranged from 3.9-5.5 mm and 10-13.2 mm, respectively. Paraffin wax (k=0.346 W/mK16) was chosen as a medium for its thermal conductivity (k) similar to that of human skin (Epidermis: k=0.209 W/mK, Dermis: k=0.310 W/mK). The surface of the phantom was prepared with a coat of matte black paint to give a surface emissivity ($\varepsilon$) of ($\varepsilon$=0.9518), similar to human skin ($\varepsilon$=0.97619). Imaging of the phantom was performed at stimulation times ranging from 500-10,000 ms and thermal recording analyzed between 0 and 30 seconds post-stimulus to optimize parameters for skin imaging.

Animal Model

All animal experimentation performed was approved by the MedStar Health Research Institute Institutional Animal Care and Use Committee. A total of 18 male Sprague Dawley rats (Harlan Laboratories, Frederick, Md.) were used in this study designed to assess burn conversion by ADT imaging. Animals were anesthetized with isofluorane, shaved and chemically depilated with Veet (Reckitt Benckiser, Parsippany, N.J.) before injury. Burns were created on the bilateral flank of each animal by contact with a 100° C. brass comb for 30 seconds. A subset of animals (n=6) underwent biopsy collection for the remainder of the time course, while another subset (n=6) underwent imaging. This burn is characterized by four, third-degree 20×25 mm rectangles separated by three, 5×25 mm interspaces. To assess conversion, the injury was modified to produce a less severe 15-second contact (n=3), and a more severe 45-second contact burn (n=3). Animals were anesthetized and imaged by LDI, ADT and a standard photograph before injury, and at 0, 2, 4, 6, 12, 24 and 36 hours post-injury.

ADT Imaging Device Design

The ADT imaging device (FIG. 4A) consisted of a thermal camera, data acquisition system and stimulation lamps interfacing with Matlab software (MathWorks, Natick, Mass.). A USB-6218 data acquisition system (National Instruments Austin, Tex.) controlled a transistor-transistor logic voltage gated 120V, 10 A relay (OPTO22, Temecula, Calif.) to digitally engage the stimulation lamps. The stimulation lamps consisted of six-50 W halogen bulbs (Philips Amsterdam, Netherlands) for a total energy delivery rate of 300 W. Thermal video was captured with an FM 320 focal plane array camera (ICI, Beaumont, Tex.) with 320×240 resolution. Matlab code was written to view thermal video input, engage stimulation and capture and save data.

ADT and Quantification

Stimulation lamps were positioned four inches above the surface of the burn and angled to face the center. Stimulation was applied for 6000 ms per the results of phantom testing, with image capture beginning immediately after stimulation ended. Image reconstruction was performed using a gradient analysis technique. Each pixel of each frame of video was subtracted from each of the previous frame, producing the gradient of thermal change. These gradient frames were summed for a total of five seconds of video, 150 frames at 30 frames per second to produce a resultant image. This method is quantitatively described by Equation 1. The unit is termed thermal flux, as it is a change in temperature as a function of time.

$$\text{Thermal Flux} \left(\frac{\delta T}{\delta t}\right) = \sum_{0}^{150\,frames} \frac{\Delta°\text{C.}}{\frac{1}{30}\,\text{second}} \quad \text{Equation 1}$$

ImageJ software (NIH, Bethesda, Md.) was then used to quantify the signal intensity of each of the four burn zones and three interspaces as individual regions of interest (ROI's) from reconstructed images.

Laser Doppler Imaging

Laser Doppler imaging was performed with a Moor LDI-2 laser Doppler imager (Moor Instruments Ltd., Axminster, United Kingdom). Signal intensity of ROI's were computed for each of the four burn zones and three interspaces with Moor LDI Image Analysis software, corresponding with the ADT analysis.

Histological Examination

Biopsies preserved in formalin were embedded in paraffin wax, sectioned at 6 μm on a Leica microtome (Solms, Germany) and adhered to Superfrost charged glass slides (ThermoFisher, Waltham, Mass.). Masson's trichrome staining was performed per standard protocol. Photomicrographs were captured at 5× magnification with an Axio Imager brightfield microscope (Zeiss, Jena, Germany).

Results

The following results demonstrate the capacity of ADT to directly identify burn wound conversion, as well as that of LDI to identify non-converting wounds.

Imaging Parameter Assessment

Figure 5:
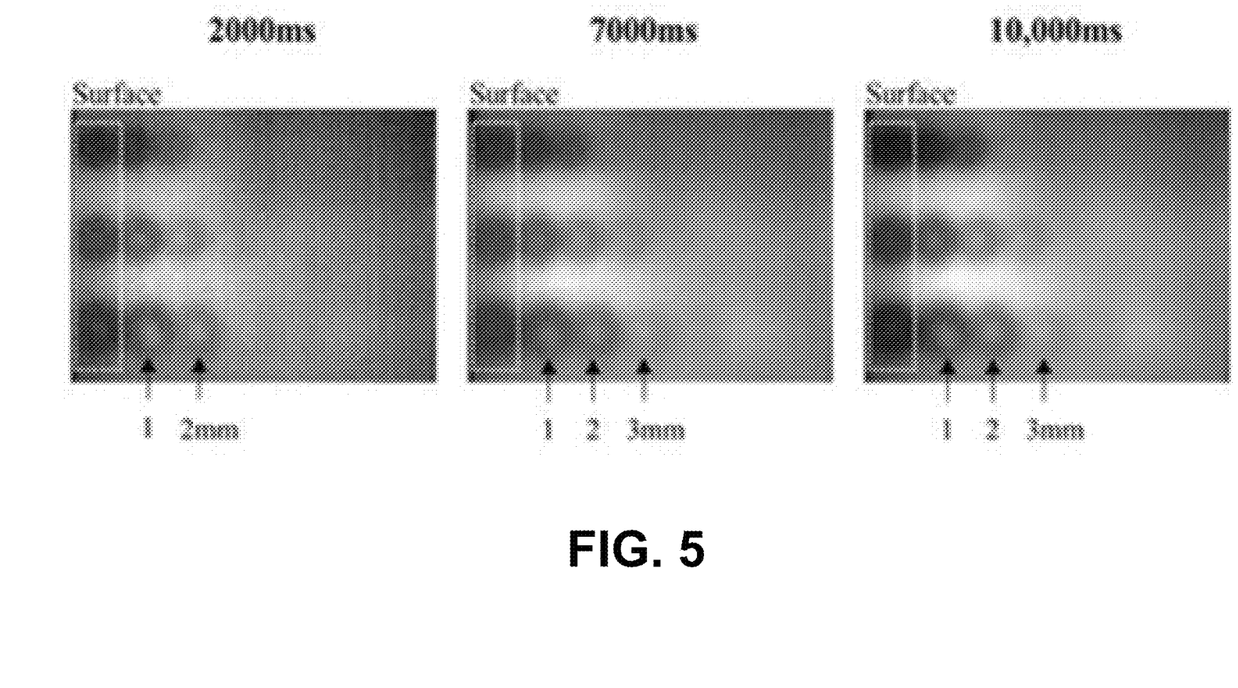
FIG. 5 is a series of pictures showing ADT imaging of a calibration skin platform with representative stimulation of 200 ms (A), 7000 ms, and 10,000 ms.
Figure 6:
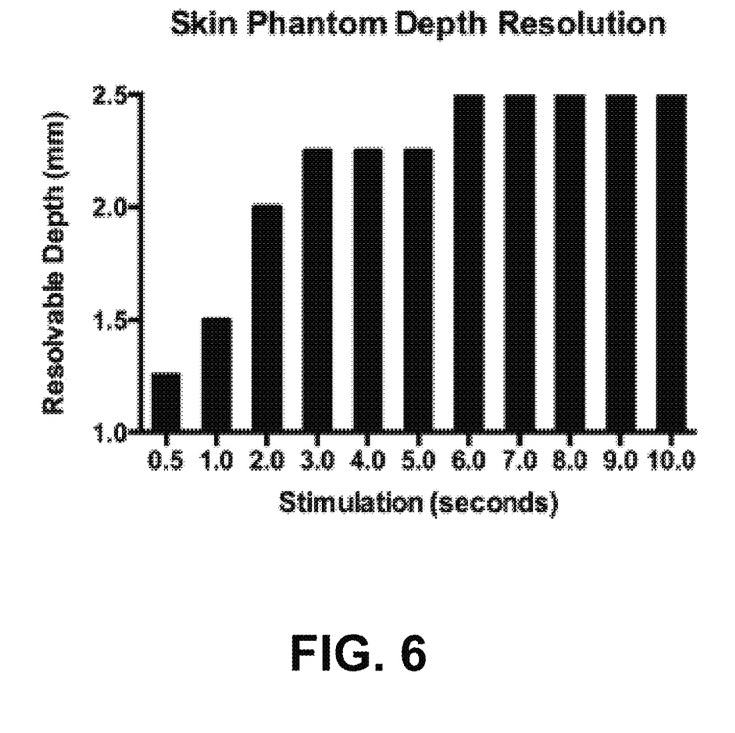
FIG. 6 is a graph showing ADT calibration imaging depth as a function of thermal stimulation.

Active dynamic thermographic imaging of the skin phantom calibrator revealed an increasing resolution of imaging depth with stimulation time (FIG. 5). Stimulation between 500 ms and 5000 ms resulted in a nearly linear increase in depth resolution, while stimulation above 6000 ms was unable to resolve any further depth due to thermal saturation (FIG. 6). A stimulation time of 6000 ms was therefore chosen as the optimal excitation parameter for this study.

Direct Thermographic and Perfusion Analysis

Figure 7:
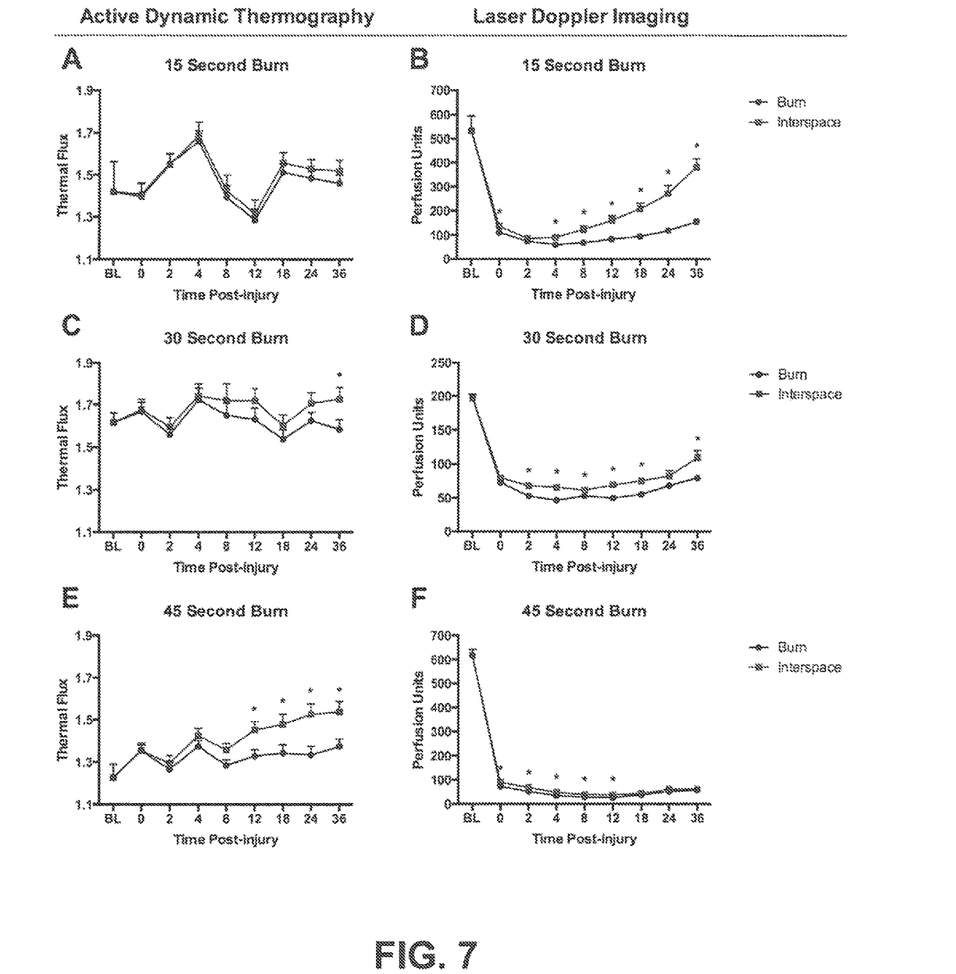
FIG. 7 includes plots showing ADT Flux thermal flux and LDI perfusion data over time for each of the 15-second, 30-second, and 45 second burn duration groups.
Figure 11:
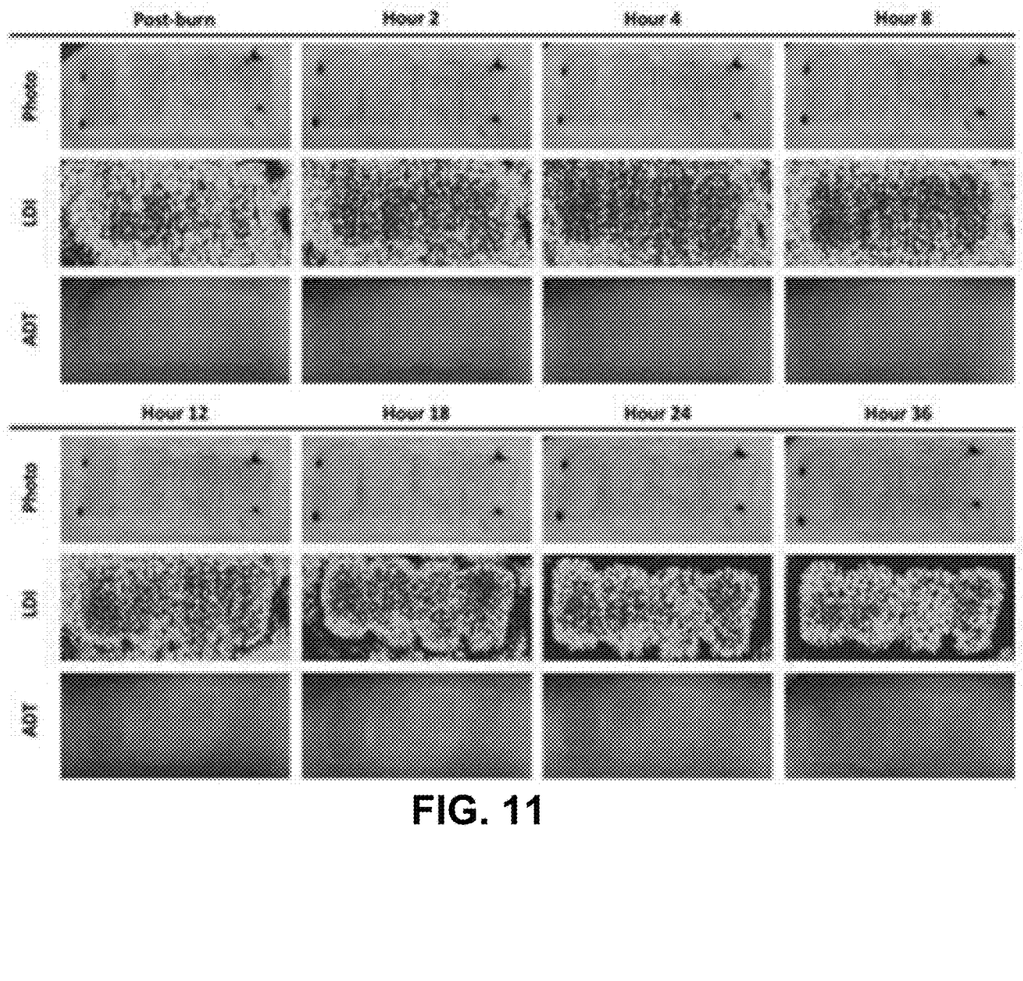
FIG. 11 shows representative photographs, laser Doppler scanning images, and active dynamic thermography gradient method reconstructed images for the 30-second burn, converting injury.

Direct analysis of thermographic and perfusion data for each burn duration (FIG. 7) revealed an inverse trend between the two imaging techniques. In the minor, 15-second burn (FIGS. 7A-B) LDI clearly depicts an increase in perfusion of the interspaces over the burn zones, while ADT shows no difference, or trend between the two. Assessment of the moderate, 30-second burn (FIGS. 7C-D) reveals a similar although minor difference between the interspaces and burn by both ADT and LDI. In the case of the severe, 45-second burn (FIGS. 7E-F) ADT clearly depicts an increasing trend in thermal flux, while LDI provides little information about the difference between the burn zone and interspace for this injury. Also see FIG. 11.

Zone of Stasis to Burn Comparison

Figure 8:
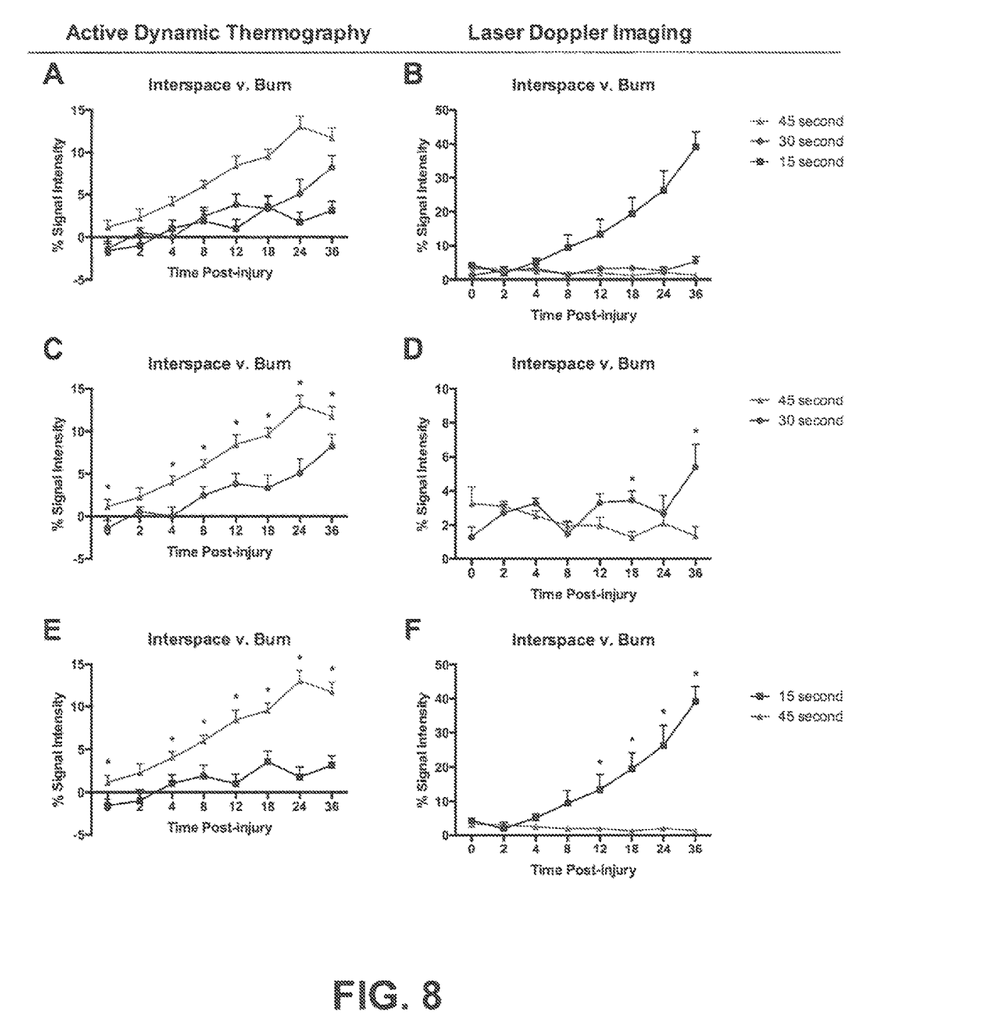
FIG. 8 includes plots showing the difference in signal between interspaces and surrounding burns for ADT and LDI.

To further characterize the ability of each imaging system to distinguish zones of stasis from burned tissue, the difference between the interspaces and burns were quantified at every time point (FIG. 8). Each interspace was compared to its adjacent burns and normalized to baseline skin to standardize units, and present both imaging systems data in terms of percentage of normal skin signal intensity. FIG. 8A illustrates the difference ADT can detect between zones of stasis and adjacent burned tissue, which follows an increasing trend with severity of the burn. LDI (FIG. 8B) contrarily depicts a large difference between the minor, 15-second burn and interspaces, but not for those of higher severity.

If the minor burn is removed from this data set (FIGS. 8C-D) it becomes clear that ADT can distinguish stasis zones from burn in both moderate and severe burns, which LDI is incapable of doing. This difference is evident ($P<0.05$) immediately following injury, and at nearly every assessment until hour 36. Likewise, if the moderate, 30 second burn is removed from this same data set (FIGS. 8E-F) it becomes apparent that while ADT is most effective at identifying zones of stasis adjacent to severe burns ($p<0.05$) post-injury to hour 36, LDI is most effective with minor burns ($p<0.05$) by hour 12.

Utility of Imaging for Identification of Burn Conversion

Figure 9:
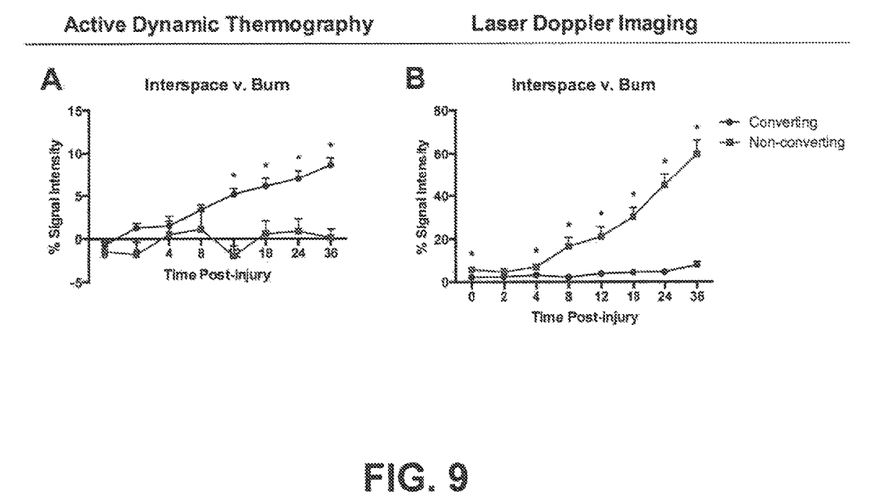
FIG. 9 includes plots showing the difference in signal between interspaces and surrounding burns for ADT and LDI, grouped as converting or non-converting burns by 48 hours.

To more clearly illustrate the differences in each imaging system for the characterization of irreversible burn progression, the data for each of the interspaces was grouped as converting or non-converting, based on visual inspection at hour 36 (FIG. 9). Perfusion imaging characterizes non-converting from converting tissue ($p<0.05$) immediately post-injury and consistently to hour 36, observing a linear increase in the difference in perfusion. Conversely, active dynamic thermography directly identifies the trend of burn conversion ($p<0.05$) by hour 12.

Histologic Examination

Figure 10:
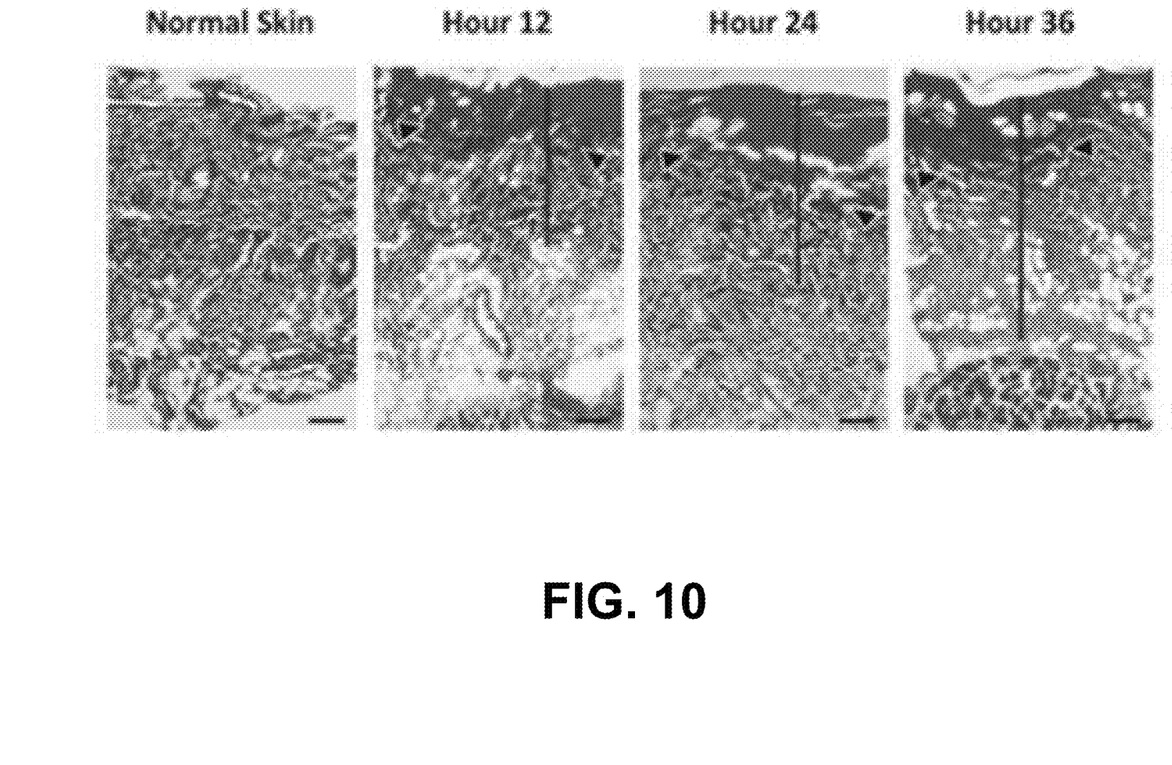
FIG. 10 shows a Masson's trichrome histological assessment of interspaces at 12-hour intervals post-burn injury with the scale bar representing 200 µm.

Conversion of the interspace tissue was confirmed by Masson's trichrome staining, which illustrates a progressing change in tissue architecture and dye affinity of the interspaces from post-burn to hour 36 (FIG. 10). Hallmarks of necrosis are apparent including complete denaturation of the epidermis and upper dermis as well as a progression of collagen denaturation into the dermis through disorganization and an exchange of dye affinity.

From the above description, those skilled in the art will perceive improvements, changes and modifications. Such improvements, changes and modifications are within the skill of one in the art and are intended to be covered by the appended claims.

What is claimed is:

1. A method comprising:
    performing non-contact imaging on a burn wound with an imaging modality configured to record imaging data, wherein the imaging modality comprises active dynamic thermography (ADT); and
    determining, by a system comprising a processor, an area of the burn wound undergoing conversion based on the imaging data,
    wherein the area of the burn wound undergoing conversion is located within a zone of stasis of the burn wound and the ADT comprises delivery of a thermal pulse to the burn wound and the imaging data relates to heat transfer for areas in the zone of stasis at different time points,
    wherein the area of the burn wound undergoing conversion exhibits a slower rate of heat transfer than the rest of the zone of stasis.

2. The method of claim 1, wherein the rate of heat transfer reflects a dissipation of the thermal pulse through a dermal capillary network and to a dermal plexus below the burn wound.

3. The method of claim 1, wherein the imaging modality further comprises laser Doppler imaging (LDI) to identify areas of the burn wound that will remain non-converting.

4. The method of claim 3, further comprising designing a targeted treatment for the burn wound based on the area of the burn wound undergoing conversion and the areas of the burn wound that will remain non-converting.

5. The method of claim 1, wherein the determining further comprises identifying structural changes in the area of the burn wound undergoing conversion based on the imaging data.

6. The method of claim 1, wherein the area of the burn wound undergoing conversion is identified within twelve hours post-burn wound.

7. An active dynamic thermography (ADT) diagnostic device comprising:
    a thermal stimulator to deliver thermal stimulation to a burn wound, wherein the thermal stimulation is a thermal pulse;
    a controller to control properties related to the thermal stimulation, wherein the properties comprise a timing parameter; and
    a receiver to receive imaging data based on the thermal stimulation of the burn wound,
    wherein the imaging data indicates an area of the burn wound undergoing conversion located within a zone of stasis of the burn wound, wherein the area of the burn wound undergoing conversion exhibits a slower rate of heat transfer than the rest the zone of stasis.

8. The diagnostic device of claim 7, wherein the timing parameter is less than 10 milliseconds.

9. The diagnostic device of claim 7, wherein the timing parameter is less than 1 millisecond.

10. The diagnostic device of claim 8, wherein the imaging data reveals a structural change in the area of the burn wound undergoing conversion compared to other areas of the zone of stasis.

11. The diagnostic device of claim 7, wherein the imaging data indicates the area of the burn wound undergoing conversion within twelve hours of a patient suffering the burn wound.

12. A system comprising:
    an imaging device to perform non-contact imaging on a burn wound with an imaging modality configured to record imaging data wherein the imaging modality comprises active dynamic thermography (ADT), wherein the ADT comprises delivery of a thermal pulse to the burn wound and the imaging data relates to heat transfer for areas in a zone of stasis at different time points;
    a computing device comprising:
        a non-transitory memory to store computer-executable instructions; and a processor to access the non-transitory memory and execute the computer-executable instructions to at least:
receive the imaging data; and
determine an area of the burn wound undergoing conversion based on the imaging data, wherein the area of the burn undergoing conversion is located within the zone of stasis of the burn wound and exhibits a slower rate of heat transfer than the rest of the zone of stasis.

13. The system of claim 12, wherein the processor further executes the computer-executable instructions to design a targeted treatment for the burn wound based on the predicted area of the burn wound undergoing conversion.

14. The system of claim 13, further comprising a surgical device to facilitate performance of a surgical procedure based on the designed targeted treatment.

15. The system of claim 12, wherein the processor further executes the computer-executable instructions to determine another area of the burn wound that will not undergo conversion based second imaging data from a second imaging modality.

* * * * *